United States Patent
Schleicher et al.

(10) Patent No.: US 10,953,155 B2
(45) Date of Patent: Mar. 23, 2021

(54) PRESSURE SENSOR IN PLUNGER HEAD TO WAKE UP ELECTRONICS

(71) Applicant: Verily Life Sciences LLC, Mountain View, CA (US)

(72) Inventors: Brett Schleicher, San Francisco, CA (US); Benjamin Krasnow, Redwood City, CA (US); Russell Mirov, Los Altos, WA (US)

(73) Assignee: Verily Life Sciences LLC, South San Francisco, CA (US)

( * ) Notice: Subject to any disclaimer, the term of this patent is extended or adjusted under 35 U.S.C. 154(b) by 391 days.

(21) Appl. No.: 15/471,358

(22) Filed: Mar. 28, 2017

(65) Prior Publication Data

US 2017/0312430 A1  Nov. 2, 2017

Related U.S. Application Data

(60) Provisional application No. 62/329,605, filed on Apr. 29, 2016, provisional application No. 62/431,774, filed on Dec. 8, 2016.

(51) Int. Cl.
*A61M 5/172* (2006.01)
*A61M 5/315* (2006.01)
(Continued)

(52) U.S. Cl.
CPC .......... *A61M 5/172* (2013.01); *A61M 5/1723* (2013.01); *A61M 5/20* (2013.01);
(Continued)

(58) Field of Classification Search
CPC ................ A61M 5/172; A61M 5/1723; A61M 5/31511; A61M 5/48; A61M 5/482;
(Continued)

(56) References Cited

U.S. PATENT DOCUMENTS

| 5,720,733 A | 2/1998 | Brown |
| 6,368,314 B1 | 4/2002 | Kipfer et al. |

(Continued)

FOREIGN PATENT DOCUMENTS

| CA | 2 604 498 A1 | 10/2006 |
| EP | 2 777 731 A1 | 9/2014 |

(Continued)

OTHER PUBLICATIONS

International Search Report and Written Opinion from the International Searching Authority dated Mar. 5, 2018, for International Application No. PCT/US2017/063768, filed Nov. 29, 2017, 16 pages.

(Continued)

*Primary Examiner* — Bhisma Mehta
*Assistant Examiner* — James D Ponton
(74) *Attorney, Agent, or Firm* — Christensen O'Connor Johnson Kindness PLLC

(57) ABSTRACT

A plunger head for a fluid injection device includes a transducer disposed in the plunger head to measure a compressive force when applied to the plunger head. The plunger head also includes a power source and a microcontroller disposed in the plunger head. The microcontroller is coupled to the power source and the transducer, and the microcontroller is coupled to enter a high-power mode in response to sensing application of the compressive force to the plunger head.

18 Claims, 5 Drawing Sheets

(51) Int. Cl.
*A61M 5/20* (2006.01)
*G01F 23/296* (2006.01)
*G01L 19/00* (2006.01)
*A61M 5/48* (2006.01)
*G01K 13/02* (2021.01)

(52) U.S. Cl.
CPC .... *A61M 5/31511* (2013.01); *A61M 5/31568* (2013.01); *A61M 5/486* (2013.01); *G01F 23/296* (2013.01); *G01K 13/02* (2013.01); *G01L 19/0092* (2013.01); *A61M 2205/33* (2013.01); *A61M 2205/332* (2013.01); *A61M 2205/3368* (2013.01); *A61M 2205/3375* (2013.01); *A61M 2205/3569* (2013.01); *A61M 2205/3584* (2013.01); *A61M 2205/3592* (2013.01); *A61M 2205/50* (2013.01); *A61M 2205/52* (2013.01); *A61M 2205/581* (2013.01); *A61M 2205/8206* (2013.01); *A61M 2205/8212* (2013.01); *A61M 2230/201* (2013.01); *G01K 2013/026* (2013.01)

(58) Field of Classification Search
CPC ...... A61M 5/484; A61M 5/486; A61M 5/488; A61M 5/31568; A61M 5/31525; A61M 2205/3368; G01L 19/0092
See application file for complete search history.

(56) References Cited

U.S. PATENT DOCUMENTS

| | | | |
|---|---|---|---|
| 8,708,957 | B2 | 4/2014 | Jespersen et al. |
| 9,314,573 | B2 | 4/2016 | Nielsen et al. |
| 9,907,902 | B2 * | 3/2018 | Mitrosky .......... A61M 5/31525 |
| 2001/0034506 | A1 | 10/2001 | Hirschman et al. |
| 2005/0258182 | A1 * | 11/2005 | Anderson ......... A61M 15/0045 221/7 |
| 2007/0060820 | A1 * | 3/2007 | Lofgren .............. A61B 5/0215 600/481 |
| 2011/0270214 | A1 | 11/2011 | Jorgensen et al. |
| 2012/0195182 | A1 | 8/2012 | Pommereau et al. |
| 2013/0072897 | A1 | 3/2013 | Day et al. |
| 2014/0288408 | A1 * | 9/2014 | Deutsch ............. A61M 16/021 600/407 |
| 2015/0165114 | A1 | 6/2015 | Grant et al. |
| 2015/0202375 | A1 | 7/2015 | Schabbach et al. |
| 2015/0217059 | A1 | 8/2015 | Ashby et al. |
| 2015/0289895 | A1 | 10/2015 | Gomi et al. |
| 2016/0022539 | A1 | 1/2016 | Daines |
| 2016/0259913 | A1 * | 9/2016 | Yu ........................ A61M 5/31 |
| 2017/0189625 | A1 * | 7/2017 | Cirillo ................... A61M 5/20 |

FOREIGN PATENT DOCUMENTS

| | | | |
|---|---|---|---|
| WO | 2007/000680 | A2 | 1/2007 |
| WO | 2007024193 | A2 | 3/2007 |
| WO | 2016/007935 | A2 | 1/2016 |
| WO | WO 2016/062605 | A1 | 4/2016 |
| WO | 2016/122974 | A1 | 8/2016 |

OTHER PUBLICATIONS

International Preliminary Report on Patentability and Written Opinion dated Oct. 30, 2018 for International Application No. PCT/US2017/023653, filed Mar. 22, 2017, 8 pages.

International Preliminary Report on Patentability and Written Opinion dated Oct. 30, 2018 for International Application No. PCT/US2017/030068, filed Apr. 28, 2017, 14 pages.

International Application No. PCT/US2017/025085—International Search Report and Written Opinion dated Jul. 17, 2017, 15 pages.

English Translation of Chinese Office Action for corresponding Chinese Patent Application No. 201790000809.1, dated Jul. 11, 2019, pp. 1-3.

Chinese Office Action with translation dated Sep. 4, 2019 in corresponding Chinese Application No. 201790000811.9, 4 pages.

* cited by examiner

PRESSURE SENSOR IN PLUNGER HEAD TO WAKE UP ELECTRONICS

REFERENCE TO RELATED APPLICATIONS

This application claims the benefit of U.S. Provisional Application No. 62/329,605, filed on Apr. 29, 2016, and U.S. Provisional Application No. 62/431,774, filed on Dec. 8, 2016, the entire contents of which are hereby incorporated by reference herein.

TECHNICAL FIELD

This disclosure relates generally to drug injection and in particular but not exclusively, relates to tracking injection quantities.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

However, even in devices that do measure dosage accurately, problems may arise from poor power management. If the device runs out of power too quickly it can no longer measure dosage.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for a pressure sensor in a plunger head to wake up electronics are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the instant disclosure, systems and methods for a "smart" plunger head are discussed. As will be shown this plunger head may be disposed within a medical syringe/cartridge and perform various operations including measuring the temperature of medication in the syringe/cartridge, emitting ultrasonic signals into the medication to calculate the quantity of medication dispensed, etc. This disclosure also relates to tactile communication with the plunger head to change its operating mode. For example, telling the plunger head to switch from a low power-mode (e.g., for power conservation) into a high-power mode (e.g., for sending and receiving ultrasonic signals, taking high frequency temperature measurements, etc). One way to achieve this communication is to include a transducer (e.g., a switch, pressure sensor, strain sensor, piezo electric, or the like) in the plunger head that, in response to a force exerted on the plunger head, informs the plunger head to switch operative modes. The following description describes several ways to implement such a plunger head.

Figure 1A:
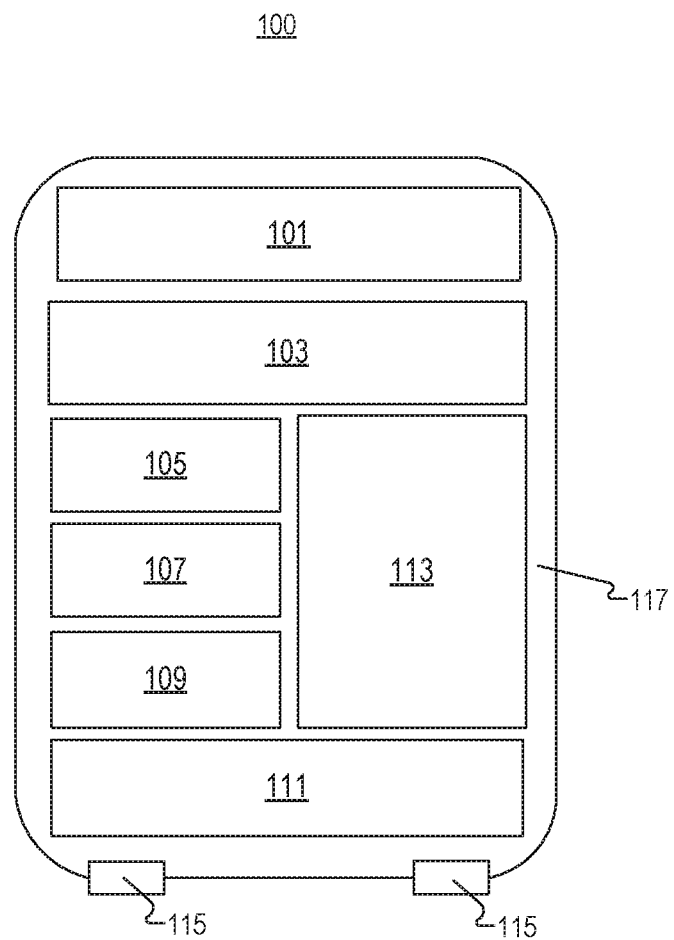
FIG. 1A illustrates a plunger head, in accordance with an embodiment of the disclosure.

FIG. 1A illustrates plunger head 100, in accordance with an embodiment of the disclosure. Plunger head 100 includes transceiver 101, power source 103, clock 105, force sensor 107 (a type of transducer), temperature sensor 109, transducer 111 (another type of transducer, depicted here to emit/receive ultrasonic signals), microcontroller 113, and electrode 115.

Transceiver 101 may include BLUETOOTH low energy (BLE) communication and may also include an antenna (e.g., for near field communication (NFC). Transceiver 101 may be configured to wirelessly communicate with a remote device (e.g., a smart phone, a glucose monitor, an insulin pump, or a computer) using one or more wireless communication methods. The one or more wireless communication methods may include, for example, radio data transmission, Bluetooth, BLE, NFC, infrared data transmission, electromagnetic induction transmission, and/or other suitable electromagnetic, acoustic, or optical transmission methods. Transducer 111 may be configured to send and receive ultrasonic signals that propagate though a syringe/cartridge containing medication. Microcontroller 113 may be programmed with instructions to control the overall operation of plunger head 100, and may be electrically coupled to every electrical device in plunger head 100. Power source 103 may be configured to power transducer 111, microcontroller 113, transceiver 101, temperature sensor 109, and other electronic components in plunger head 100.

In some embodiments, the components of plunger head 100 may be at least partially encapsulated in an elastomer 117 (e.g., rubber, ethylene propylene (EPM), Nitrile (NBR), ethylene propylene diene (EPDM), polybutadiene, or polisoprene) that is shaped to define plunger head 100.

In some embodiments, microcontroller 113 may be attached to a printed circuit board and may include one or more processors, including for example, a central processing unit (CPU). The processors may include any suitable type of commercially available processor or may be a custom design. Microcontroller 113 may include additional components, for example, non-volatile memory (e.g., a flash memory), volatile memory (e.g., a random access memory (RAM)), and other like components, configured to store information). Microcontroller 113 may be programmed with logic that when executed by microcontroller 113, cause other pieces of circuitry to perform operations. More specifically microcontroller 113 may be used to control the operation of transducer 111. Microcontroller 113 may be programmed with instructions to calculate data representative of the quantity of medication dispensed from a syringe or cartridge where plunger head 100 resides. For example, in some embodiments, microcontroller 113 may be programmed to detect and record the reflection times of ultrasonic signals emitted and received by transducer 111. Based on the reflection times, microcontroller 113 may track and produce a time profile of the position of transducer 111 (i.e., plunger head 100). Based on the time profile of the position, microcontroller 113 may be able to identify a first distance D1 or starting position (e.g., before the medication is dispensed), which may correspond with the cartridge/syringe barrel being filed and a second distance D2 or ending position (e.g., after the medication is dispensed), which may correspond with the barrel being empty. Microcontroller 113 may then calculate the change in distance between D1 and D2 and based on of the change in distance may calculate the volume (i.e., amount or quantity) of medication dispensed.

In some embodiments, plunger head 100 may also have clock 105 including a crystal oscillator configured to keep a real time clock (RTC) so that the date and time of each injection may be accurately recorded and stored in memory of microcontroller 113. Crystal oscillator may be, for example, a 32 KHZ crystal oscillator. In some embodiments, microcontroller 113 may include an internal oscillator (e.g., RC oscillator), which may be calibrated using the crystal oscillator. The internal RC oscillator may be, for example, a 10 MHZ RC oscillator. Internal RC oscillator may provide sufficient time accuracy to measure the position (e.g., distance D) of plunger head 100 to within, for example, about 150 microns. In some embodiments, transducer 111 may be used as an oscillator or as a calibrator for the internal RC oscillator. In some embodiments, the frequency of the RC oscillator may be up-converted on microcontroller 113 to a higher frequency. For example, the RC oscillator may be used to drive a higher-frequency phase-locked loop.

In some embodiments, plunger head 100 may be designed to back-interpolate the time of each injection enabling crystal oscillator to be eliminated. In order to maintain the RTC, crystal oscillator may consume a significant amount of power, thus eliminating the crystal oscillator can save a significant amount of power as well as save space.

In some embodiments, plunger head 100 may also include a force sensor 107 (a type of transducer). Force sensor 107 may be configured to detect when a force is applied to plunger head 100 by a plunger or the like. Force sensor 107 may be, for example, a simple spring-loaded switch that is molded into the plunger head 100. In some embodiments, transducer 111 may be configured to function as a force sensor thereby eliminating the need for a separate force sensor 107. For example, transducer 111 may have a piezoelectric element that may detect the dynamic changes in pressure when a user depresses a plunger in the syringe (e.g., FIG. 2A) or injection pen system (e.g., FIG. 2B).

Power source 103 may be any suitable power source. For example, power source 103 may be a battery, a capacitor, or the like. In some embodiments, power source 103 may be rechargeable via wireless energy transmission, for example, inductive coupling, resonant inductive coupling, radio frequency (RF) link, or the like. In some embodiments, power source 103 may be a non-rechargeable battery that is configured to last the storage and operational life of plunger head 100.

In some embodiments, plunger head 100 may also include electrodes 115 (connected to microcontroller 113) that are configured to measure the conductivity of medication. In some embodiments, the electrodes 115 may protrude out from the surface of plunger head 100 where the electrodes 115 may contact the medication. With the density, conductivity, and viscosity of the medication determined, microcontroller 113 may have a sufficient number of properties to profile the medication (e.g., chemical composition, percent degradation etc.).

Figure 1B:
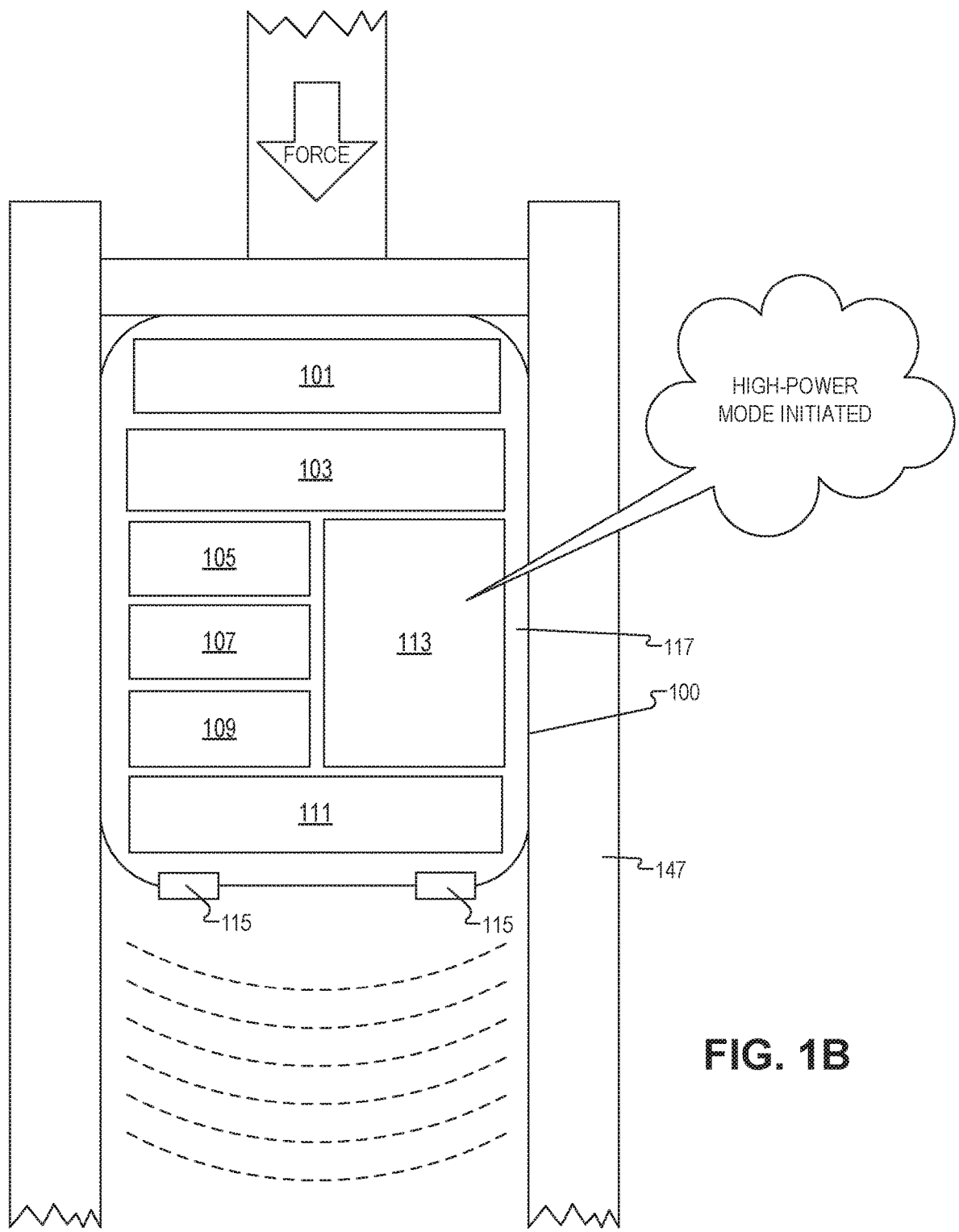
FIG. 1B illustrates exerting a force on the plunger head of FIG. 1A, in accordance with an embodiment of the disclosure.

FIG. 1B illustrates exerting a force on plunger head 100 of FIG. 1A, in accordance with an embodiment of the disclosure. As shown, plunger head 100 is disposed either in a syringe body 147 (see e.g., FIG. 2A) or a cartridge body 147 (see e.g., FIG. 2B), and one side of plunger head 100 is contacted by a plunger of the syringe/injection pen. In the depicted embodiment, the plunger is exerting a downward force on plunger head 100. A transducer (e.g., force sensor 107 or transducer 111) is disposed in the plunger head 100 to measure the compressive force from the plunger when the force is applied to plunger head 100. As depicted, microcontroller 113 is disposed in plunger head 100 and is electrically coupled to power source 103 and the transducer so that microcontroller 113 enters a high-power mode in response to the compressive force applied to plunger head 100. This is because the transducer is coupled to microcontroller 113 to output a signal to microcontroller 113 indicative of the compressive force. The transducer may register a binary or analog force signal.

In one embodiment, (e.g., where force sensor 107 is the transducer) the transducer will only activate high-power mode in microcontroller 113 if the compressive force applied is above a threshold value. In other embodiments, prior to receiving the compressive force there is no electrical contact between power source 103 and microcontroller 113, and in response to the compressive force, the force sensor couples microcontroller 113 and power source 103 to initiate the high-power mode (e.g., by flipping a switch or the like). In this embodiment, the power conservation mode may be an off-state. In other words, power source 103 may be positioned such that when no compressive forces are applied to plunger head 100, there is no electrical contact between power source 103 and the electronic components in plunger head 100, thereby keeping the other electronic components powered down (i.e., conserving power). But when compressive forces are applied to plunger head 100, power source 103 or one or more of the other electronic components may be moved and brought into electrical contact, thereby powering up plunger head 100. In some embodiments, power source 103 may be positioned within plunger head 100, such that the compressive force applied by the plunger depicted acts as an on/off switch, which initiates (e.g., wakes up or powers up) the electronic components of plunger head 100.

In other embodiments, plunger head 100 includes a plurality of operative modes including the power conservation mode and the high-power mode, and microcontroller 113 causes plunger head 100 to transition between the plurality of operative modes in response to a unique force profile. The unique force profile may include applications of force in rapid succession (e.g., pressing down on the syringe three times), an extended application of force (e.g., holding pressure on the syringe for several seconds or more), pressing exceptionally hard on the syringe or any other uniquely identifiable signal. Force may be applied when a cap or stopper prevents fluid form leaving the syringe or cartridge, or may occur when the syringe/cartridge is free to dispense liquid. For example a unique force profile could be the force profile of fluid being injected into a person (e.g., the specific pressure/resistance encountered when fluid is being pushed into a vein/artery). Alternatively, the unique force profile could be the force profile associated with an "air shot"—a pre injection release of medication to clear debris/air bubbles—which signifies to plunger head 100 that an injection is about to take place. However one of ordinary skill in the art will appreciate that there are many other unique force profiles that may trigger electrical activity in plunger head 100.

In some embodiments, the plurality of operative modes include at least one of an off-state, a low frequency temperature measurement state, a high frequency temperature measurement state (where the measurement frequency of the low frequency temperature measurement state is less than that of the high frequency temperature measurement state), a fluid quantity measurement state, and a data transfer state. Accordingly, plunger head 100 may be received by the user in a low frequency temperature measurement state, where plunger head 100 measures the temperature of the fluid (medication in the syringe/cartridge) with temperature sensor 109 while microcontroller 113 is in the power conservation mode. For example, when sent out from the factory, plunger head 100 may be set to a low-power low-frequency temperature measurement state that periodically takes the temperature of the medication to make sure there was no spoilage during delivery to the user (in low power mode, plunger head 100 may also check the conductivity of the medication in a similar way). However, once the cartridge/syringe is purchased by the user, the user may activate plunger head 100 in the cartridge/syringe by applying a unique force profile to plunger head 100. When this occurs, plunger head 100 may switch to high-power mode, where plunger head 100 sends and receives ultrasonic signals, takes high frequency temperature measurements, measures the electrical conductivity of the medication, or measures clicks from the injection pen (in an insulin pen embodiment of the disclosure), transmits and receives collected data, etc.

In one embodiment, transducer 111 is coupled to both emit ultrasonic signals and receive/measure the compressive force. However, in other embodiments a second dedicated transducer (e.g., force sensor 107) is coupled to microcontroller 113 to receive the compressive force.

In the depicted embodiment, when plunger head 100 receives the compressive force, it begins to send and receive ultrasonic signals/waves. As shown, plunger head 100 is disposed in the body 147 of a cartridge or syringe. Through the emission of the ultrasonic signals, microcontroller 113 is able to calculate a quantity of a fluid in the fluid injection device when plunger head 100 is inserted in the fluid injection device (e.g., the cartridge or syringe). In the depicted embodiment sending and receiving the ultrasonic signals from plunger head 100 includes sending the ultrasonic signals along a length of the fluid injection device (e.g., in a direction substantially parallel to the walls defining body 147), reflecting the ultrasonic signals back towards plunger head 100 (from a surface that may be at least partially parallel to the surface of plunger head 100 that emits the ultrasonic signals), and receiving the ultrasonic signals with transducer 111 or the second transducer.

It is common for goods, including medical injection devices, to have a long storage life between the time of manufacture and time of use/sale. In products that include embedded electronics, in particular a battery, it can be a challenge to conserve battery power while the products are in storage. Some products have no on/off switch, buttons, or removable/rechargeable batteries, so the traditional approach of disconnecting or turning off the device while in storage may not be feasible. Also, certain products (e.g., medical injection devices) that include perishable goods (e.g., medication) it may be advantageous to have the product monitor the storage environment (e.g., temperature, light, etc.) and log or store this data and this can't be done if the battery is disconnected.

To address this challenge, plunger head 100 may be designed to enter a low-power sleep mode while in storage. Plunger head 100 may be programmed to enter low-power sleep mode as part of the manufacturing and testing process for plunger head 100 or the medication injection device. When in low-power sleep mode the rate of power consumption may be a fraction of the rate of power consumption for normal operation. While in low-power sleep mode, microcontroller 113 may be programmed with instructions to periodically wake up to measure the temperature. Microcontroller 113 may also log the temperature to create a temperature history. Alternatively, in some embodiments microcontroller 113 may be programmed to log the temperature only when there is a change in temperature, thus saving on data storage. The efficacy of some medications is affected by temperature. For example, insulin is sensitive to hot and cold temperatures. Plunger head 100 thus may monitor the temperature of the medication through storage and up through use to ensure it stays within an acceptable range. If the temperature of the medication goes outside the acceptable range then plunger head 100 may be configured to send an alert. As stated before, plunger head 200 may be put in this low power state, or taken out of this low power state, by applying a force to plunger head 200, in accordance with the teachings of the present disclosure.

Figure 2A:
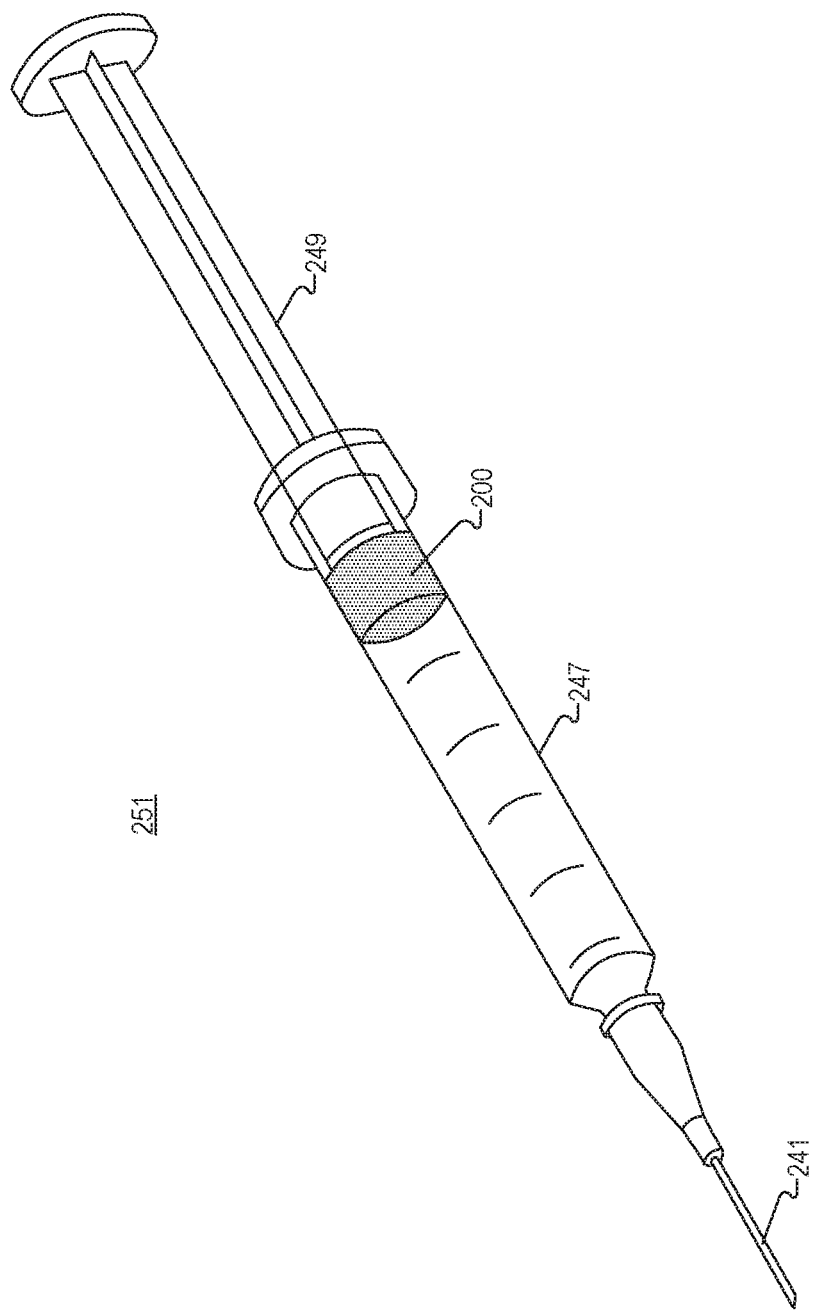
FIG. 2A is an illustration of the plunger head of FIG. 1A in a syringe, in accordance with an embodiment of the disclosure.

FIG. 2A is an illustration of plunger head 200 of FIG. 1A in a syringe 251, in accordance with an embodiment of the disclosure. As illustrated "smart" plunger head 200 may have been placed in body 247 of syringe 251 in order to measure dosage, temperature of the medication, conductivity of the medication or the like. Plunger head 200 may be installed in a standard syringe 251 by withdrawing plunger 249, removing the standard plunger head, and installing smart plunger head 200. In some embodiments, syringe 251 may be manufactured and supplied with a smart plunger head 200 preinstalled. Plunger head 200 may be sized to correspond with the size of body 247. For example, plunger head 200 may be formed to fit any size syringe 251. Needle 241 may come preinstalled or be attached by the user.

In the depicted embodiment, when the user presses down on plunger, plunger head 200 may register this compressive force and switch from a power conservation (low-power) mode to a high-power mode or vice versa depending on the type of pressure applied (e.g., if the pressure single is uniquely identifiable as an "on" signal). Plunger head 200 may perform different or additional functions (e.g., emitting ultrasonic signals) when it switches from power conservation mode to high-power mode.

Figure 2B:
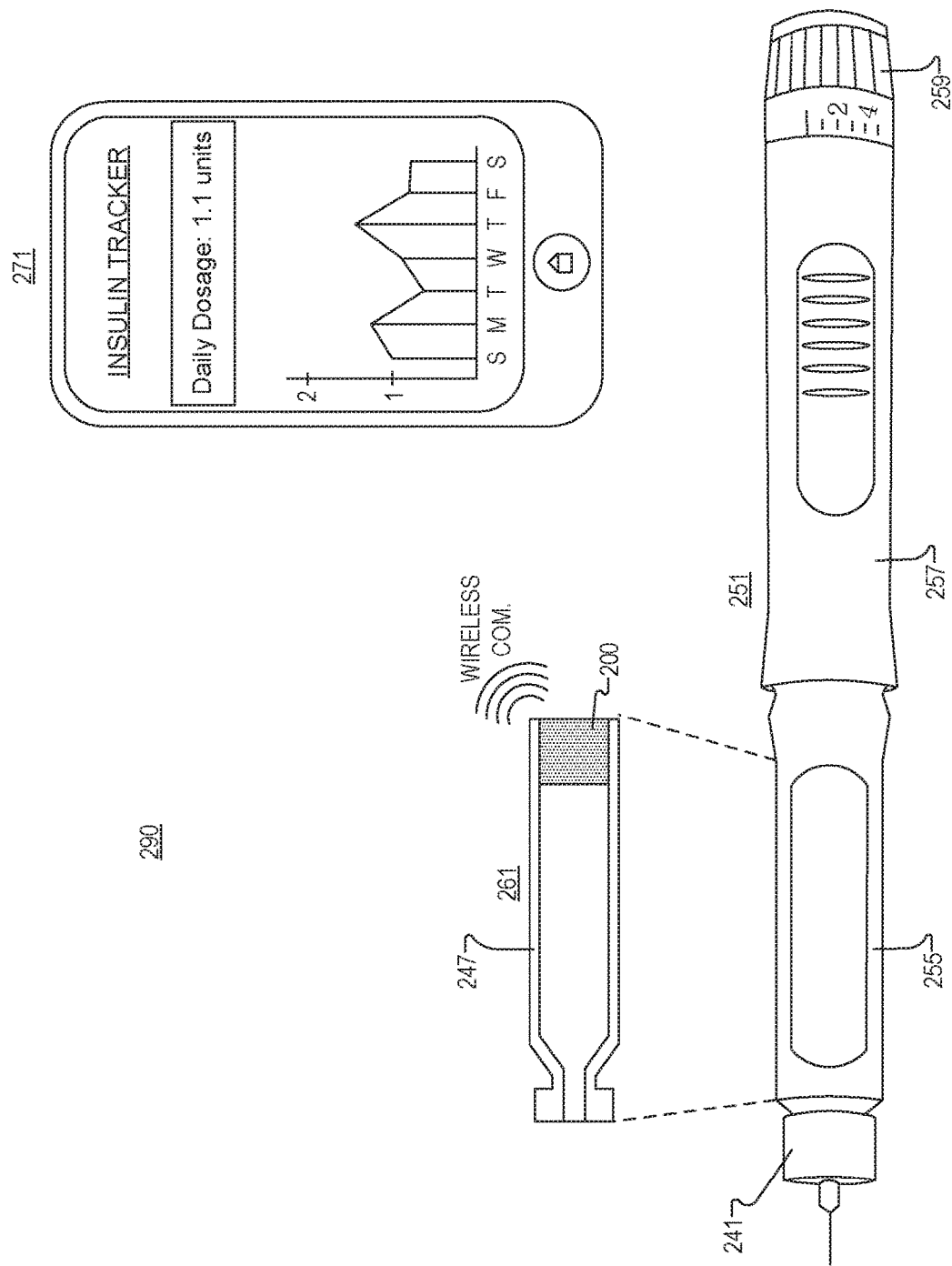
FIG. 2B is an illustration of the plunger head of FIG. 1A in a cartridge for an injection pen system, in accordance with an embodiment of the disclosure.

FIG. 2B is an illustration of the plunger head 200 of FIG. 1A in a cartridge 261 for an injection pen system 290, in accordance with an embodiment of the disclosure. Pen system 290 includes drug cartridge 261, injection pen 251, and processing device 271 (e.g., a smart phone).

Drug cartridge 261 includes cartridge body 247, and plunger head 200. In the depicted embodiment, plunger head 200 starts near the rear of drug cartridge 261 and is pushed forward in drug cartridge 261 (with a plunger in pen 251) to expel medication/fluid from the narrow end of drug cartridge 261. Plunger head 200 may come pre-installed in drug cartridge 261, or may be swapped in by a user. Similar to other embodiments, plunger head 200 may be supplied in a power conservation mode, and then when pressure is exerted on plunger head 200, it may switch to a high-power mode. In power conservation mode, plunger head 200 (or more specifically the electronics in plunger head 200) may measure the temperature of the fluid in drug cartridge 261, medication conductivity, or the like. In high-power mode, plunger head 200 may emit ultrasonic signals into the drug cartridge 261 to measure an amount of medication in drug cartridge 261. Alternatively or additionally, when plunger head 200 is in high-power mode, plunger head 200 may measure pen "clicks" (indicative of the amount of medication the user selects to dispense from the pen 251) with a piezoelectric device or the like.

Injection pen 251 is a hand-held device and includes needle 241, chamber 255 (to hold drug cartridge 261), body 257 (including a drug dispensing actuator—"plunger"—to push in plunger head 200 and extract fluid from drug cartridge 261), and a drug delivery control switch 259 (twist the switch to "click" control the dosage). However, as one of ordinary skill in the art will appreciate, injection pen 251 can take other configurations and have other components. It is appreciated that injection pen 251 may be a generic store-bought pen, and that drug cartridge 261 is configured to fit in most generic pens.

Processing device 271 (e.g., a smartphone, tablet, general purpose computer, distributed system, servers connect to the internet, or the like) may be coupled to receive data from drug cartridge 261 to store/analyze this data (either when plunger head 200 is in power conservation mode or high-power mode). For instance, in the depicted embodiment, processing device 271 is a smartphone, and the smartphone has an application running recording how much insulin has been spent from pen 251. Moreover the application is plotting how much insulin has been injected by the user over the past week.

Figure 3:
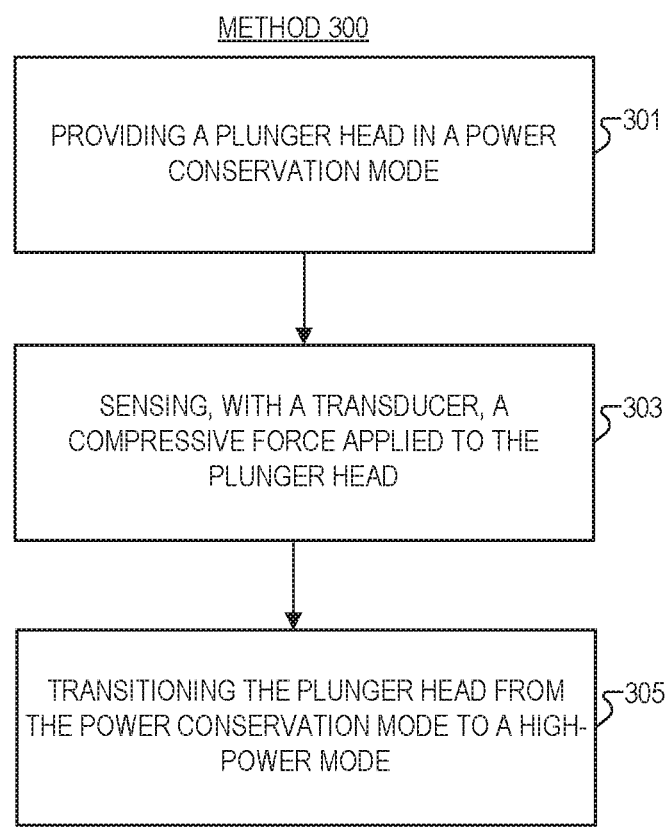
FIG. 3 is a method to control electronics in a plunger head for a fluid injection device, in accordance with an embodiment of the disclosure.

FIG. 3 illustrates a method 300 to control electronics in a plunger head for a fluid injection device, in accordance with an embodiment of the disclosure. The order in which some or all of process blocks 301-305 appear in method 300 should not be deemed limiting. Rather, one of ordinary skill in the art having the benefit of the present disclosure will understand that some of method 300 may be executed in a variety of orders not illustrated, or even in parallel. Further, blocks may be added or removed from method 300 in accordance with the teaching of the present disclosure.

Block 301 shows providing the plunger head in a power conservation mode. In other words, at the beginning of method 300 the plunger head starts in the power conservation mode. As in other embodiments, the plunger head may include a microcontroller and a transducer, where the transducer is coupled to the microcontroller. In one embodiment, the plunger head may measure the temperature of the medication with a temperature sensor (disposed in the plunger head) while the plunger head is in the power conservation mode. One of ordinary skill in the art will appreciate that the plunger head may also be able measure conductivity, send and receive ultrasonic signals, and the like when in power conservation mode.

Block 303 illustrates receiving, with the transducer, a compressive force applied to the plunger head. Most commonly this will be the plunger from an injection device pressing on the plunger head when a user decides to switch-on the plunger head or change the operational state of the plunger head (e.g., from a low power "conservation" mode to a high-power mode). Pressing on the plunger to initiate this transition from power conservation mode to high-power mode may occur when the device is delivered to the user, or by the user when an injection is about to take place. In some embodiments, different modes may be initiated at different times, for instance a low power temperature measurement mode may be initiated when the plunger head leaves a factory because the transport conditions are known (e.g., refrigerated truck or the like) and thus measurement only needs to occur infrequently, but when the cartridge/syringe containing the plunger head is received by a retail store or a user, a high frequency mode is initiated since storage conditions are unknown (e.g., the temperature of the user's medicine cabinet). Therefore the device may need to measure temperature more frequently to avoid spoilage.

Block 305 shows transitioning the plunger head from the power conservation mode to a high-power mode, where the high-power mode consumes more power than the power conservation mode. In one embodiment, when the plunger head enters the high-power mode, it emits and receives ultrasonic signals from at least one of the transducer or a second transducer disposed in the plunger head. In some embodiments, the plunger head may further calculate a quantity of fluid in the fluid injection device in response to emitting and receiving the ultrasonic signals. In another or the same embodiment, the power conservation mode and the high-power mode are merely two modes in a plurality of operative modes, and in response to a unique force profile (included in the compressive force) the plunger head will switch between individual modes in the plurality of operative modes. In some embodiments, the same unique force profile (e.g., three presses in succession) will switch plunger head between all of the modes; however, in other embodiments different force profiles may switch the plunger head into a unique mode of operation (e.g., three presses for high-power mode, and one long press to emit ultrasonic signals).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A plunger head for a fluid injection device, comprising:
a transducer disposed in the plunger head to output a signal when a compressive force is applied to the plunger head, wherein the signal is indicative of the compressive force;
a power source disposed in the plunger head;
a temperature sensor disposed in the plunger head to measure a temperature of a fluid in the fluid injection device; and
a microcontroller, disposed in the plunger head, coupled to the power source, the transducer, the temperature sensor, and a memory, the memory including instructions that when executed by the microcontroller causes the plunger head to perform operations including:
transition between individual modes included in a plurality of operative modes of the plunger head in response to the microcontroller receiving the signal output by the transducer, wherein the plurality of operative modes includes a power conservation mode, a high-power mode, a low frequency temperature measurement state, and a high frequency temperature measurement state, wherein the plunger head consumes more power when in the high-power mode relative to when the plunger head is in the power conservation mode; and
periodically measure the temperature of the fluid with the temperature sensor when the plunger head is in either the low frequency temperature measurement state or the high frequency temperature measurement state, wherein a measurement frequency of the low frequency temperature measurement state is less than that of the high frequency temperature measurement state.

2. The plunger head of claim 1, wherein there is no electrical contact between the power source and the microcontroller when the plunger head is in the power conservation mode.

3. The plunger head of claim 2, wherein the transducer includes a force sensor, and wherein the signal output by the transducer is indicative of a force profile included in the compressive force, and wherein in response to the compressive force the force sensor couples the microcontroller and the power source to initiate transition of the plunger head to the high-power mode based on the force profile.

4. The plunger head of claim 3, wherein the power conservation mode is an off-state.

5. The plunger head of claim 1, wherein the transition of the plunger head between the individual modes included in the plurality of operative modes of the plunger head is based on a force profile included in the compressive force and measured by the transducer, and wherein the force profile corresponds to at least one of application of forces in succession to the plunger head or an extended application of force to the plunger head.

6. The plunger head of claim 1, wherein the memory includes additional instructions that when executed by the microcontroller causes the plunger head to perform further operations including:
identify one of different force profiles as being included in the compressive force applied to the plunger head based on the signal output by the transducer; and
transition to one of the plurality of operative modes of the plunger head based on the identified one of the different force profiles.

7. The plunger head of claim 6, wherein the plurality of operative modes further include at least one of an off-state, a fluid quantity measurement state, or a data transfer state.

8. The plunger head of claim 1, wherein the transducer or a second transducer is coupled to the microcontroller to send and receive ultrasonic signals, and wherein the memory includes additional instructions that when executed by the microcontroller causes the plunger head to perform further operations including:
send and receive the ultrasonic signals with at least one of the transducer or the second transducer when the plunger head is in the high-power mode.

9. The plunger head of claim 8, wherein the memory includes additional instructions that when executed by the microcontroller causes the plunger head to perform further operations including:
calculate a quantity of the fluid in the fluid injection device when the plunger head is inserted in the fluid injection device, in response to the sending and receiving of the ultrasonic signals, and
wherein sending and receiving the ultrasonic signals includes sending the ultrasonic signals along a length of the fluid injection device, reflecting the ultrasonic signals back towards the plunger head, and receiving the ultrasonic signals with the transducer or the second transducer.

10. A drug delivery system to inject a fluid, comprising:
a vessel including an interior cavity to hold the fluid;
a plunger disposed in the drug delivery system to exert a compressive force on a plunger head; and
the plunger head disposed in the interior cavity to expel the fluid from the vessel in response to the compressive force from the plunger, the plunger head including:
a transducer disposed in the plunger head to output a signal when the compressive force is exerted on the plunger head, wherein the signal is indicative of the compressive force;
a power source disposed in the plunger head;
a temperature sensor disposed in the plunger head to measure a temperature of the fluid in the vessel; and
a microcontroller, disposed in the plunger head, coupled to the power source the transducer, the temperature sensor, and a memory, the memory including instructions that when executed by the microcontroller causes the drug delivery system to perform operations including:
    transition the plunger head between individual modes included in a plurality of operative modes of the plunger head in response to the microcontroller receiving the signal output by the transducer, wherein the plurality of operative modes includes a power conservation mode, a high-power mode, a low frequency temperature measurement state, and a high frequency temperature measurement state, wherein the plunger head consumes more power when in the high-power mode relative to when the plunger head is in the power conservation mode; and
    periodically measure the temperature of the fluid with the temperature sensor when the plunger head is in either the low frequency temperature measurement state or the high frequency temperature measurement state, wherein a measurement frequency of the low frequency temperature measurement state is less than that of the high frequency temperature measurement state.

11. The drug delivery system of claim 10, wherein there is no electrical contact between the power source and the microcontroller when the plunger head is in the power conservation mode.

12. The drug delivery system of claim 10, wherein the transducer includes a force sensor, and wherein the signal output by the transducer is indicative of a force profile included in the compressive force, and wherein the memory includes additional instructions that when executed by the microcontroller causes the drug delivery system to perform further operations including:
    transition the plunger head between the plurality of operative modes in response to the compressive force including the force profile, wherein the force profile corresponds to at least one of application of forces in succession to the plunger head or an extended application of force to the plunger head.

13. The drug delivery system of claim 10, wherein the memory includes additional instructions that when executed by the microcontroller causes the drug delivery system to perform further operations including:
    identify one of different force profiles as being included n the compressive force exerted on the plunger head based on the signal output by the transducer; and
    transition to one of the plurality of operative modes of the plunger head based on the identified one of the different force profiles.

14. The drug delivery system of claim 10, further comprising a wireless transmitter, wherein the memory includes additional instructions that when executed by the microcontroller causes the drug delivery system to perform further operations including:
    instruct the wireless transmitter to transmit data including the temperature of the fluid.

15. A method implemented by a plunger head for a fluid injection device, comprising:
    sensing, with a transducer, a force applied to the plunger head to generate a signal indicative of the force, wherein the plunger head includes a microcontroller, a power source, a temperature sensor, and the transducer, wherein the microcontroller is coupled to the transducer to receive the signal; and
    transitioning the plunger head between individual modes included in a plurality of operative modes of the plunger head in response to the microcontroller receiving the signal from the transducer, wherein the plurality of operative modes includes a power conservation mode, a high-power mode, a low frequency temperature measurement state, and a high frequency temperature measurement state, wherein the plunger head consumes more power when in the high-power mode relative to when the plunger head is in the power conservation mode; and
    periodically measuring a temperature of a fluid in the fluid injection device when the plunger head is in either the low frequency temperature measurement state or the high frequency temperature measurement state, wherein a measurement frequency of the low frequency temperature measurement state is less than that of the high frequency temperature measurement state.

16. The method of claim 15, further comprising emitting and receiving ultrasonic signals from at least one of the transducer or a second transducer disposed in the plunger head when the plunger head is in the high-power mode.

17. The method of claim 16, further comprising calculating a quantity of fluid in the fluid injection device in response to emitting and receiving the ultrasonic signals.

18. The method of claim 15, wherein the transitioning the plunger head between the individual modes included in the plurality of operative modes of the plunger head is based on a force profile included in the compressive force and measured by the transducer, and wherein the force profile corresponds to at least one of application of forces in succession to the plunger head or an extended application of force to the plunger head.

\* \* \* \* \*